(12) United States Patent  
Lee et al.

(10) Patent No.: US 6,873,165 B2  
(45) Date of Patent: Mar. 29, 2005

(54) NEAR-FIELD PROBE FOR USE IN SCANNING SYSTEM

(75) Inventors: Jongjoo Lee, Suwon-si (KR); Jungho Kim, Daejeon (KR)

(73) Assignee: Korea Advanced Institute of Science and Technology (KAIST), Daejeon (KR)

( * ) Notice: Subject to any disclaimer, the term of this patent is extended or adjusted under 35 U.S.C. 154(b) by 30 days.

(21) Appl. No.: 10/395,284

(22) Filed: Mar. 25, 2003

(65) Prior Publication Data

US 2003/0184328 A1 Oct. 2, 2003

(30) Foreign Application Priority Data

Mar. 26, 2002 (KR) .................. 10-2002-0016564

(51) Int. Cl.⁷ ..................... G01R 31/302; G01R 31/308
(52) U.S. Cl. ........................ 324/750; 324/753
(58) Field of Search ................ 324/750, 752, 324/753, 158.1; 385/16, 17; 250/306, 307

(56) References Cited

U.S. PATENT DOCUMENTS 5,416,327 A * 5/1995 Weiss et al. ................ 250/307
5,936,237 A * 8/1999 van der Weide ............ 250/234

* cited by examiner

*Primary Examiner*—David Zarneke
*Assistant Examiner*—Russell M. Kobert
(74) *Attorney, Agent, or Firm*—Jones Day

(57) ABSTRACT

A near electric-field probe is driven by a short laser pulse delayed through an optical delay-line for detecting vectors of near-field components of electrical signals propagating through a device under test including an electrical device or an electronic circuit based on a sampling principle. The near-field probe includes a photoconductive switch assembly including a thin semiconductor photoconductive body, at least two separated switch electrodes formed on the thin semiconductor photoconductive body, and an electrode gap formed between the two separated switch electrodes; and an optical waveguide attached to one side of the photoconductive switch assembly by using an optical adhesive, wherein the optical waveguide is partially coated with conductive material on the outer surface thereof.

22 Claims, 11 Drawing Sheets

NEAR-FIELD PROBE FOR USE IN SCANNING SYSTEM

BACKGROUND OF THE INVENTION

1. Field of the Invention

The present invention relates to a scanning system, and more particularly, to an near electric-field probe capable of measuring vectorial electric field by using short optical pulse and an ultrafast photoconductive switch.

2. Description of the Prior Art

Continuing advances in the development of novel materials and modern semiconductor devices/circuits have pushed the operating frequency of quantum-electronic and opto-electronic devices/circuits over multi-hundred gigahertz frequency region and have brought the millimeter-wave circuits into real world. The integrity of the devices/circuits in turn is becoming more and more increasing. On the other hand, high-speed devices/circuits have been facing unexpected phenomena and problems related to electromagnetic field therein. Accordingly, needs for a novel diagnostic system to cope with those kind of phenomena and problems are also increasing. Moreover, there have been needs not only for diagnosis for electrical characteristics of the devices/circuits but for spectroscopic technologies reaching even far infra-red region in order to give a diagnosis of various electric and optical characteristics of materials.

One of the most popular methods for the diagnosis is to measure near-field with high spatial resolution. A probe or detector for use in measuring the near electric-field is required to have wide range of bandwidth and high temporal resolution for measuring various frequency components as well as to be small enough to detect field at any measured point. Also required are a flexible polarization and a high sensitivity(signal to noise ratio) to achieve precise measurement. In addition, a loading effect and an invasiveness should be low enough to minimize the distortion due to the detector or the peripheral devices with respect to a device under test(DUT).

Since 1980s, a variety of scanning probe microscopes such as a scanning tunnel microscope(STM), a scanning force microscope(SFM) and a scanning optical mocroscope (SOM) have been developed. Such scanning probe microscopes have a spatial resolution up to a degree of elements, and therefore, are feasible for measurement of ultrafast high-integrated devices/circuits. The electrical measurement frequencies of such microscopes are limited depending on the electronic parts employed therein. For instance, they exhibit rather low measurement sensitivity due to a tunneling current introduced thereto as for the STM, due to deviation of a cantilever as for the SFM, and due to exploiting an evanescent-wave coupling as for the SOM.

In an effort to overcome the reduction in the measurement bandwidth and low measurement sensitivity resulting from employment of these peripheral devices, a photoconductive sampling technology has been developed, in which picosecond electrical signals are measured by introducing short optical pulses into an ultrafast photoconductive switch. The photoconductive sampling technology has advantages that it can measure sub-picosecond signals with high sensitivity by exploiting low frequency devices. The photoconductive sampling technology involves a photoconductive switch which is a kind of a metal-semiconductor-metal(MSM) photodetector. If a laser beam with short pulse duration(e.g., a laser beam having less than 100 fs can be generated using the mode-locked Ti:Sapphire laser) is introduced to the photoconductive switch, carriers are generated in the photoconductive region of the photoconductive switch. Measured signals can be detected from the behavior of the carriers which display the behavior in conformity to the electrical signal under measurement. An electrical pulse with very narrow duration may be generated when the lifetime of the carriers is very short. Herein, a photoconductor having carriers exhibiting very short lifetime is called an ultrafast photoconductive body. LT-GaAs(Low-temperature-grown GaAs) and SOS(Silicon-on-Sapphire) are examples of the ultrafast photoconductive body, especially with carriers having lifetime of sub-picoseconds. There may be two methods for measuring electrical signals with resolution of sub-picoseconds on the basis of a photoconductive sampling principle. One is a pump-probe measurement(PPM) and the other is a time-equivalent sampling(TES).

According to the PPM, a short pulse laser beam generated from a laser is splitted into two beams: a pump laser pulse beam and a probe laser pulse beam. The pump laser pulse beam is introduced onto a first ultrafast photoconductive switch(or photodetector) to generate an electrical pulse signal, while the probe laser pulse beam is introduced to a second ultrafast photoconductive switch via a fine translation stage or an optical delay-line, to detect the electrical pulse signal generated at the first photoconductive switch. Herein, where a device under test(DUT; e.g., electrical device or circuit) is placed in-between the first photoconductive switch and the second photoconductive switch, the second photoconductive switch may present an impulse response of the DUT in response to input of the electrical pulse signal from the first photoconductive switch, wherein the impulse response is regarded as a measured signal. The measured signal includes a signal presenting cross-correlation between the electrical pulse from the second photoconductive switch and the to-be-measured signal with respect to a time delay between the pump laser pulse beam and the probe laser pulse beam. That is, the second ultrafast photoconductive switch measures electrical characteristics of the DUT by sampling electrical signal proportional to the to-be-measured signal from a time delay of the first ultrafast photoconductive switch.

As described above, the PPM is basically a method for measuring pulse response. The TES, on the other hand, is a method for measuring ultra high frequency signal operating with respect to a single frequency in the steady state. The TES requires synchronization between repetition rate of laser pulse beams($f_{laser}$) and the operating frequency($f_m$) of the DUT. In other words, signal $f_{IF}=ABS(f_m-n \cdot f_{laser})$ obtained by mixing the electrical signal $f_{laser}$ obtained by introducing laser pulses to the first photoconductive switch (or photodetector) and to-be-measured signal with frequency of $f_m$, is used for triggering a lock-in amplifier(or an oscilloscope or a spectrum analyzer). Then, sampling the electrical signal by activating the second ultrafast photoconductive switch with another probe laser pulse beam generated at the laser, results in signals equivalent to the to-be-measured signal at the frequency of $f_{IF}$.

Measurement of electrical signal by the photoconductive sampling method was first proposed by D. H. Auston, and this method is also called an "On-wafer Measurement Method." FIG. 1 is a schematic diagram of a set-up for measuring electrical signal propagating on a conducting line by using the photoconductive sampling method. The on-wafer measurement method employs a photoconductive switch to be used as an electrical pulse signal generator 110 and an electrical signal detector 120. More specifically, the conducting line and a first photoconductive switch 110 connected thereto are placed on the ultrafast photoconductive body and dc voltage is applied to the first photoconductive, switch 110, a pump laser pulse beam generated from a short pulse laser system 140 is applied thereto in order to generate the electrical pulse signal propagated through the conducting line, consecutively a probe laser pulse beam is guided to pass through an optical delay-line before being applied to a second photoconductive switch 120 and a third photoconductive switch (not shown, but positioned at the side of the electrical signal generator 110), and finally, the electrical signal passing through or being reflected from the DUT may be detected. Therefore, according to the on-wafer measurement method, electrical characteristics of the DUT which are positioned between photoconductive switches may be detected. In order to overcome disadvantages of the on-wafer measurement method that the photoconductive switches must be associated with the DUT on the ultrafast photoconductive body, the photoconductive switches are associated with electrical contact probe to measure electrical characteristics of an DUT. This method, however, still bears limitations that it can measure only a resultant scalar voltage/current not a vectorial component which collectively constitutes electromagnetic wave.

Another exemplary method on the basis of the photoconductive sampling principle is a terahertz system. A so-called terahertz radiation refers to a phenomenon that when short laser pulse is introduced onto a photoconductive switch biased with dc voltage, not only electrical pulse signal is generated and propagated through an electrical line connected to the photoconductive switch in the wake of generated carriers and but also electromagnetic wave which is the derivative of the electrical pulse signal is radiated. A system exploits the terahertz radiation is called terahertz system. A terahertz signal radiated from a terahertz transmitter is measured by the photoconductive sampling principle in order to identify characteristics of various materials and to perform imaging(also called a terahertz imaging), wherein the terahertz transmitter introduces laser pulse beam onto a photoconductive switch biased with dc voltage to radiate terahertz wave and another photoconductive switch positioned on the ultrafast photoconductive body through an optical delay-line detects the responsive terahertz wave.

FIG. 2 is a schematic diagram of the terahertz system. As shown in FIG. 2, a pump laser pulse beam generated from the short pulse laser system 240 is introduced to a transmitter including a first photoconductive switch 210 which is biased with dc voltage in order to generate terahertz electromagnetic wave, and on the other hand, a probe laser pulse beam is introduced to a receiver including a second photoconductive switch 220 through the optical delay-line 250 to measure the terahertz electromagnetic wave. A terahertz electromagnetic wave that has been radiated from the first photoconductive switch 210 of the transmitter and then transmitted through or reflected on the DUT 230 is measured by the second photoconductive switch 220 of the receiver. Accordingly, the electrical characteristics of the DUT 230 positioned between the terahertz transmitter 210 and the terahertz receiver 220 can be measured. The terahertz system, however, also bears limitations that it exhibits rather low spatial resolution and is inappropriate for use in near-field measurement due to relatively large sizes of the transmitter/receiver and due to various auxiliary devices for collecting the radiated terahertz electromagnetic wave.

Meanwhile, when carriers are generated by introducing short laser pulse to unbiased ultrafast photoconductive switch placed in the free space, the carriers displays movements affected by ambient electromagnetic field. The movement of the carriers solely depends on the component of the electromagnetic field that is parallel to the ultrafast photoconductive switch. Accordingly, components of electromagnetic field can be distinctively observed under the photoconductive sampling principle employing the ultrafast photoconductive switch.

SUMMARY OF THE INVENTION

An object of the present invention is to provide an electric near-field probe capable of conducting direct measurement of the electric field component inside a high-speed device under test by using a photoconductive sampling principle utilizing short optical pulse and ultrafast photoconductive switches.

Another object of the present invention is to provide a terahertz electromagnetic wave radiator and measurement probe for use as a terahertz transmitter and a terahertz receiver in a terahertz system.

Yet another object of the present invention is to provide a manufacturing method of a probe for near-field measurement.

According to an aspect of the present invention, there is provided A near-field probe driven by a short laser pulse delayed through an optical delay-line for detecting vectors of near-field components of electrical signals propagating through a device under test including an electrical device or an electronic circuit based on a sampling principle, comprising: a photoconductive switch assembly including a thin semiconductor photoconductive body, at least two separated switch electrodes formed on the thin semiconductor photoconductive body, and an electrode gap formed between the two separated switch electrodes; and an optical waveguide attached to one side of the photoconductive switch assembly by using an optical adhesive, wherein the optical waveguide is partially coated with conductive material on the outer surface thereof, wherein the conductive material forms at least two parallel stripe electrodes in the longitudinal direction of the optical waveguide, and the stripe electrodes are electrically connected to each other with the switch electrodes and a core of the optical waveguide is optically aligned with the electrode gap.

According to another aspect of the present invention, there is provided An array near-field probe driven by a short laser pulse delayed through an optical delay-line for detecting vectors of near-field components of electrical signals propagating through a device under test including an electrical device or an electronic circuit based on a sampling principle, the array near-field probe including M by N (M and N are integers larger than 1) array of near-field probes, wherein each near-field probe includes: a photoconductive switch assembly including a thin semiconductor photoconductive body, at least two separated switch electrodes formed on the thin semiconductor photoconductive body, and an electrode gap formed between the two separated switch electrodes; and an optical waveguide attached to one side of the photoconductive switch assembly by using an optical adhesive, wherein the optical waveguide is partially coated with conductive material on the outer surface thereof, wherein the conductive material forms at least two parallel stripe electrodes in the longitudinal direction of the optical waveguide, and the stripe electrodes are electrically connected to each other with the switch electrodes and the core of the optical waveguide is optically aligned with the electrode gap.

According to yet another aspect of the present invention, there is provided A method for manufacturing a near-field probe, comprising the steps of: (a) growing or depositing a sacrificial layer on a semiconductor substrate; (b) growing or depositing an epilayer of a thin photoconductive body on the sacrificial layer; (c) forming two separated switch electrode patterns by using a photoresistor on the epilayer; (d) forming a photoconductive switch with an electrode gap between the two separated switch electrode patterns by depositing a metal electrode on each of the switch electrode patterns; (e) removing the photoresistor and the unnecessary metal except the switch electrodes by lift-off process; (f) forming a desired pattern of a photoconductive switch assembly by selectively etching the epilayer; (g) detaching the photoconductive switch assembly from the semiconductor substrate by using a chemical etching solution; and (h) forming the near-field probe by associating the photoconductive switch assembly with one end of an optical waveguide by using an optical adhesive, wherein the optical waveguide is coated with a conductive material, the conductive material is coated on the outer surface of the optical waveguide in the longitudinal direction thereof to form two parallel stripe electrodes, the stripe electrodes and a core of the optical waveguide are aligned to switch electrodes and the electrode gap of the photoconductive switch assembly.

BRIEF DESCRIPTION OF THE DRAWINGS

The above and other objects and features of the present invention will become apparent from the following description of a preferred embodiment given in conjunction with the accompanying drawings, in which.

DETAILED DESCRIPTION OF THE INVENTION

Hereinafter, a preferred embodiment of the present invention will be described in detail with reference to the accompanying drawings.

Figure 3:
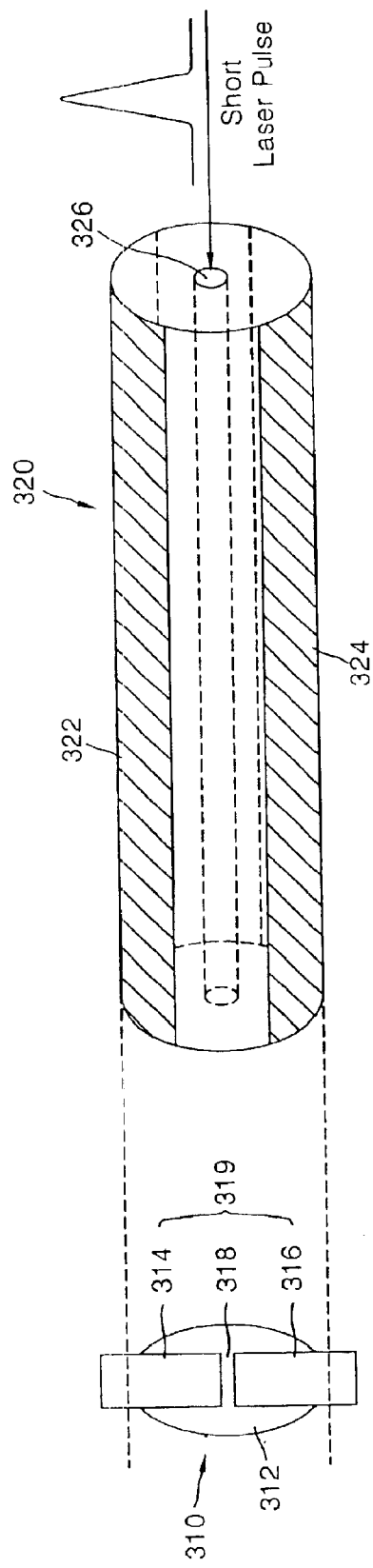
FIG. 3 illustrates a near-field probe for use in measuring tangential electric field component in accordance with a first preferred embodiment of the present invention.

FIG. 3 illustrates a near-field probe for use in measuring tangential electric field component in accordance with a first preferred embodiment of the present invention.

The inventive near-field detector comprises a photoconductive switch assembly 310 and an optical waveguide 320 placed by one side of the photoconductive switch assembly 310.

The photoconductive switch assembly 310 includes a thin ultrafast photoconductive body, at least two switch electrodes 314 and 316 separated from each other formed on the thin ultrafast photoconductive body and an electrode gap 318 between the separated switch electrodes 314 and 316.

The thin ultrafast photoconductive body 312 has a carrier lifetime of around picosecond or shorter and composed of materials capable of absorbing wavelength of short laser pulse. For instance, the thin ultrafast photoconductive body 312 uses LT-GaAs or SOS where the laser wavelength is less than or equal to 840 nm but uses InGaAs where the laser wavelength is less than or equal to 1.6 micrometer. The switch electrodes 314 and 316 of the photoconductive switch 319 are preferably made of such materials that could withstand an HF solution such as used in thin-film removal, e.g., Chromium(Cr) or Gold(Au). The switch electrodes, however, may be made of any metal as long as they are protected by coating with material such as wax.

Meanwhile, the optical waveguide 320 is made of an optical fiber or a dielectric waveguide, and on the outer surface thereof is partially coated by two stripes of conductive material in the longitudinal direction, the conductive material forming two stripe electrodes 322 and 324. The stripe electrodes 322 and 324 is made of, e.g., a conductive epoxy. Short laser pulse generated from such as a mode-locked Titanium:Sapphire laser or a mode-locked fiber optic pulse laser is introduced to a core 326 or the center of the optical waveguide.

The photoconductive switch assembly 310 is attached on one end of the optical waveguide 320 with an adhesive for optical use. The photoconductive switch assembly 310 may be connected either to a side on which the photoconductive switch 319 is formed or to the other side on which the photoconductive switch 319 is not formed. As the adhesive for binding the optical waveguide 320 and the photoconductive switch assembly 310, a ultraviolet adhesive is used since the short laser pulse can pass through it. The refraction coefficient of the ultraviolet adhesive is preferably smaller than that of the thin photoconductive body 312 and greater than that of the optical waveguide 320. When the optical waveguide 320 and the photoconductive switch assembly 310 are bound, two stripe electrodes 322 and 324 of the optical waveguide 320 are aligned with two electrodes 314 and 316 of the photoconductive switch 319, and at the same time, the core 326 of the optical waveguide 320 is aligned with the electrode gap 318 of the photoconductive switch 319. The two stripe electrodes 322 and 324 of the optical waveguide 320 and the two electrodes 314 and 316 of the photoconductive switch 319 which are aligned with each other, are electrically connected through a conductive adhesive such as a conductive epoxy.

In the present invention, though the cross-section of the optical waveguide 320 is illustrated as a circle, it may be formed as rectangle or other shapes.

Figure 1:
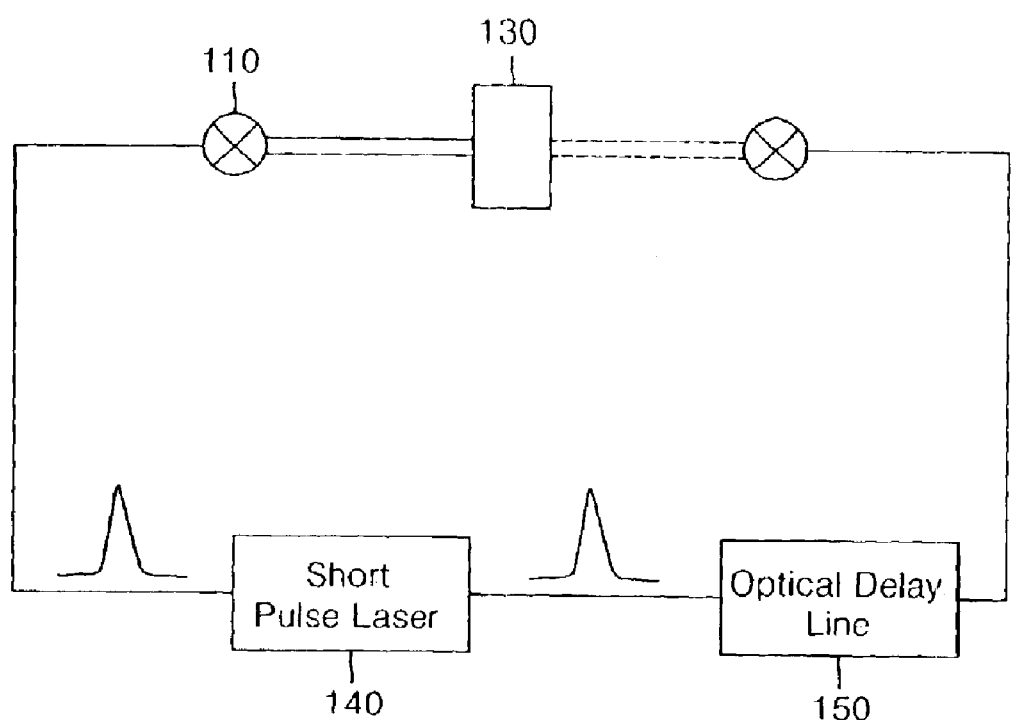
FIG. 1 is a schematic diagram of a set-up for measuring electrical signal propagating on a conducting line by using the photoconductive sampling method.
Figure 2:
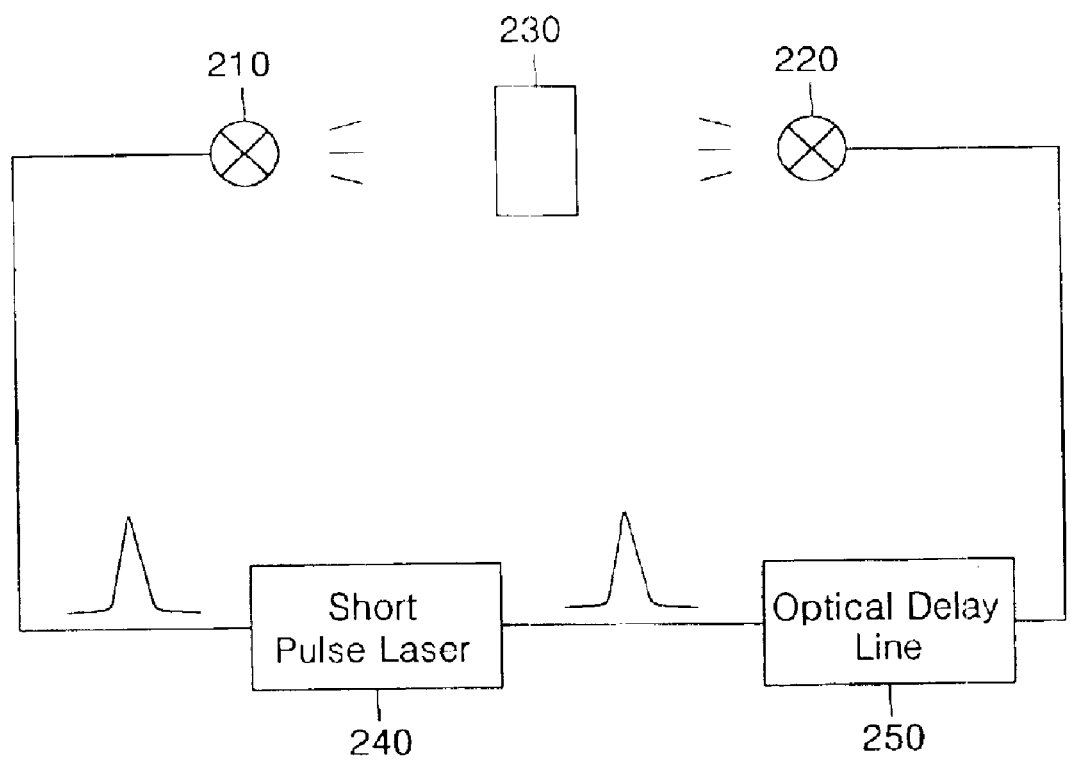
FIG. 2 is a schematic diagram of the terahertz system.

The inventive probe of FIG. 3 is used for measuring tangential component of the near-field with respect to the DUT, i.e., transverse and longtudinal component of the near-field. If the inventive probe is used with a moving stage in the X, Y and Z direction or a three-dimensional scanning system with respect to the electrical signal detector 120 of FIG. 1, it can be used in producing a three-dimensional near-field map. If, however, a DC bias is applied and laser pulse is irradiated to the ultrafast photoconductive switch 319, the terahertz radiation occurs. Referring to FIG. 2 and FIG. 3, by implementing a terahertz system with a terahertz transmitter and a terahertz receiver and by introducing an electromagnetic pulses from the terahertz system to various materials, characteristics of the various materials can be measured. In addition, it can be used in constituting images of the DUT by associating the probe in accordance with the present invention with the moving stage making a non-contact move in the X- or Y-direction or the two-dimensional scanning system. Therefore, the probe illustrated in FIG. 3 is capable of performing terahertz imaging, measuring far field components as well as performing imaging through the measurement of the near-field components.

Figure 4:
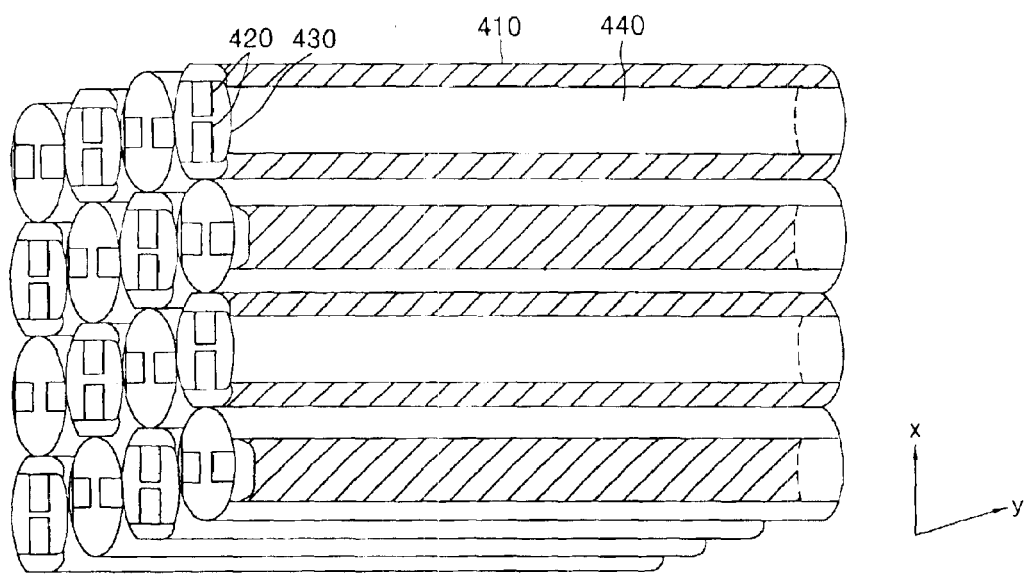
FIG. 4 illustrates a constitution of an array probe in accordance with the second preferred embodiment of the present invention.

FIG. 4 illustrates a constitution of an array probe in accordance with the second preferred embodiment of the present invention.

The array probe illustrated in FIG. 4 is an array including M by N number (M and N are integers) of the near-field probes that is illustrated in FIG. 3. In the array probe of FIG. 4, each probe includes the photoconductive switch assembly 430 consisting of the photoconductive switch 420 and the optical waveguide attached to one end of the photoconductive switch assembly 430 as shown in FIG. 3. Therefore, detailed description as to the photoconductive switch assembly 430 and the optical waveguide are omitted herein.

If each probe 410 is arranged perpendicular to each photoconductive switch 420, it can be used as a two-dimensional tangential field components measuring array probe since it separately measures near-field component in the X-direction and Y-direction at the same time.

In addition, the array probe in accordance with the present invention, by applying DC voltage and introducing laser pulse to each ultrafast photoconductive switch 420, is capable of causing the terahertz radiation, and capable of inducing terahertz radiation by applying DC voltage to a single probe among the array probe and measuring reflected terahertz electromagnetic waves by utilizing the remaining probes. Therefore, provided the terahertz system employing two array probes are used, it is capable of measuring both the terahertz electromagnetic wave reflected from the DUT and the terahertz electromagnetic wave transmitting through the DUT, which ensures obtaining an image.

Figure 5:
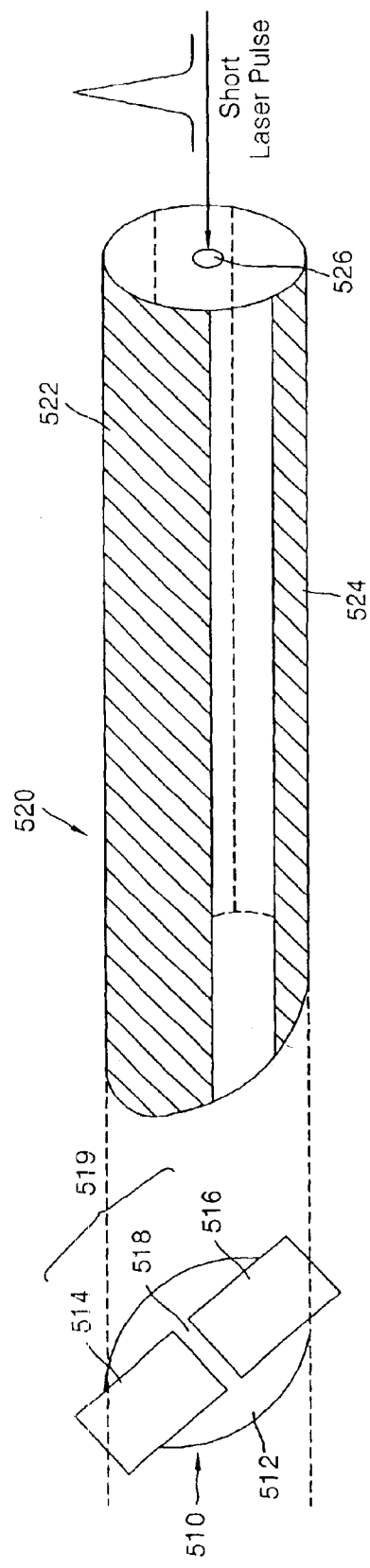
FIG. 5 shows a near-field probe in accordance with the third preferred embodiment of the present invention.

FIG. 5 shows a near-field probe in accordance with the third preferred embodiment of the present invention.

The near-field probe in FIG. 5 includes, like the near-field probe illustrated in FIG. 3, the photoconductive switch assembly 510 consisting of the ultrafast photoconductive body 512 and the photoconductive switch 519, and the optical waveguide 520 attached to one end of the photoconductive switch assembly 510 with the optical adhesive. Unlike the near-field probe in FIG. 3, however, in the near-field probe in FIG. 5, the cross-section of one end of the optical waveguide 520 is inclined, e.g., 45 degrees, and the photoconductive switch assembly 510 is attached on this cross-section by using the optical adhesive.

The outer view of the incline of the optical waveguide 520 is an oval figure when a circular optical fiber is used as the optical waveguide, and in consequence, the switch assembly 510 attached to the incline is also of the oval figure. When bound by the optical adhesive, the core 526 of the optical waveguide 520 and the electrode gap 518 of the photoconductive switch 519 should be aligned, and at the same time, the two stripe electrodes 522 and 524 of the optical waveguide 520 and the two switch electrodes 524 and 526 of the photoconductive optical switch 519 should be electrically connected.

The probe in accordance with the third preferred embodiment of the present invention has advantages that it can measure not only the two-dimensional tangential component of electromagnetic field but also the three-dimensional vector including a normal component of the electromagnetic field. For the purpose of a near-field measurement, the probe should be positioned 45 degrees inclined with respect to the DUT.

Figure 6:
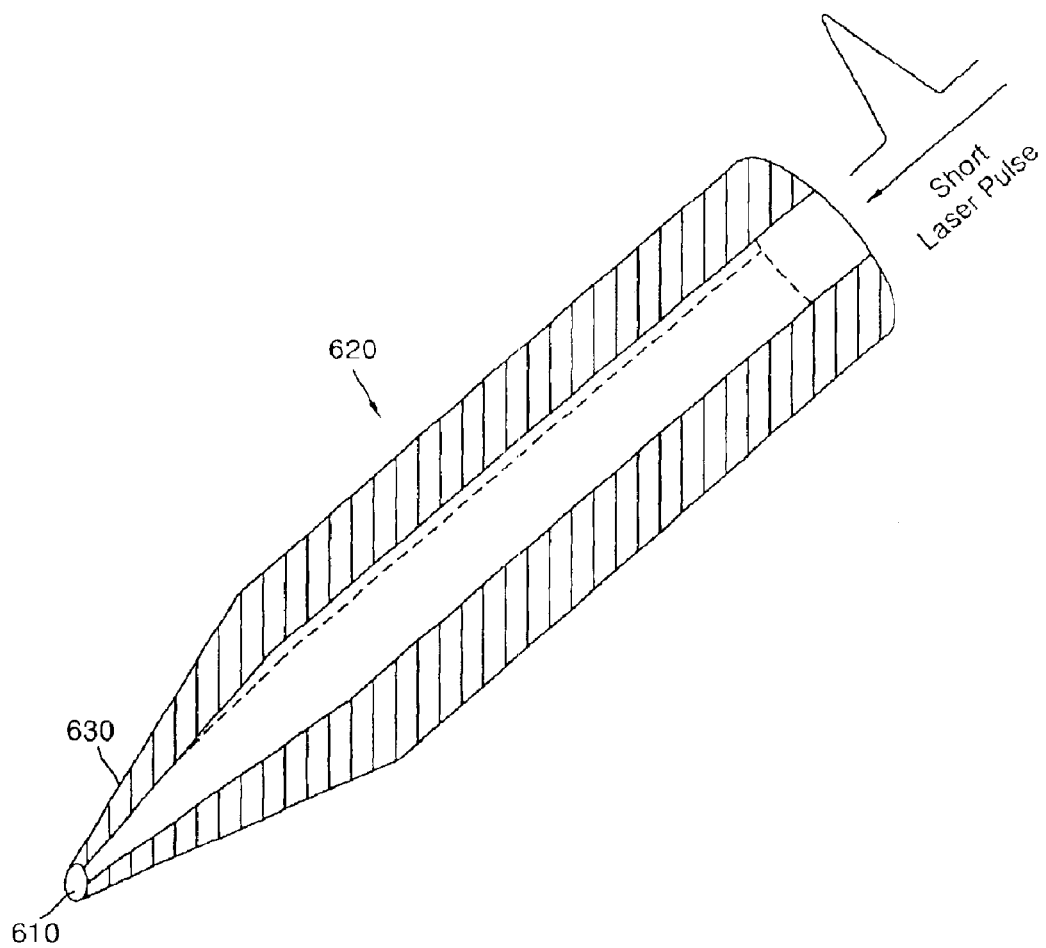
FIG. 6 describes a near-field probe in accordance with a fourth preferred embodiment of the present invention.

FIG. 6 describes a near-field probe in accordance with a fourth preferred embodiment of the present invention.

The near-field probe in FIG. 6 includes, like the near-field probe illustrated in FIG. 3, the photoconductive switch assembly 610 and the optical waveguide 620 attached to one end of the photoconductive switch assembly 610 with the optical adhesive. Unlike the near-field probe in FIG. 3, as for the near-field probe in FIG. 6, one end of the optical waveguide 620 is tapered by a prescribed tapering angle to form a bevel-edge 630 and the tip of the bevel-edge 630 is inclined like the near-field probe of FIG. 5. The inclined angle of the tip of the bevel-edge 630 is 45 degrees for measuring three-dimensional right-angled intersection components, and further, the inclined angle of the taper of the bevel-edge 630 should be smaller than or equal to 45 degrees. Therefore, the inclined surface of the optical waveguide 620 is of oval figure when circular optical fiber is used, and accordingly the photoconductive switch assembly 610 attached to the inclined surface is also of oval figure, though the size is very small.

The near-field probe in accordance with the fourth preferred embodiment of the present invention has a constitution that the optical waveguide 620 is cut or polished as the form of the bevel-edge 630 and the tip thereof is polished to be inclined so, and very small ultrafast photoconductive switch assembly 610 is attached thereto. Therefore, it is capable of separately measuring each near-field component in each of the X-, Y- and Z-direction near the DUT in the order of several micrometers, and in consequence, is capable of measuring three-dimensional vectors. Herein, the probe should be positioned relative to the DUT with 45 degrees.

FIGS. 7a to 7k provide a fabricating process for the near-field probe shown in FIGS. 3 to 6. The fabricating process may be applied to the near-field probe that exploits a LT-GaAs epilayer as an active photoconductive film.

Figure 7A:
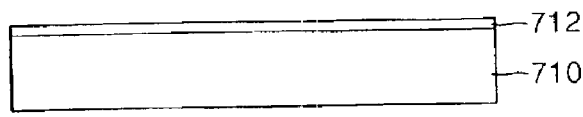
FIGS. 7a to 7k provide a fabricating process for the near-field probe.

First, as shown in FIG. 7a, a substrate 710, e.g., SI-GaAs substrate is prepared, and then, a sacrificial layer 712 is layered atop the substrate. Herein, the sacrificial layer 712 is a selective-etching material such as AlAs, and a few tens of nanometers would be enough for the thickness of the sacrificial layer 712.

Figure 7B:
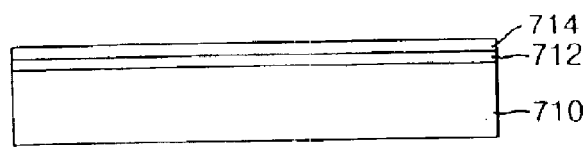

As a next step, as shown in FIG. 7b, a thin ultrafast photoconductive body is formed on the sacrificial layer 712 with thickness of 100 nanometers to 2 micrometers by growing a photoconductive epilayer 714. The photoconductive epilayer 714 is formed by growing GaAs when AlAs is used as the sacrificial layer 712 or by growing InGaAs when InP is used as the sacrificial layer 712. The sacrificial layer 712 is utilized for isolating the photoconductive epilayer 714 from the substrate 710, as described later.

Figure 7C:
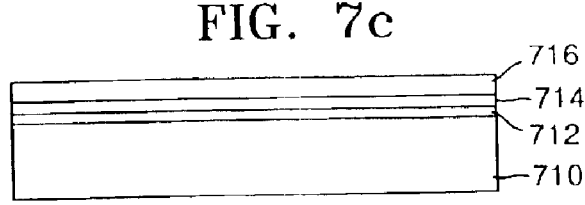
Figure 7D:
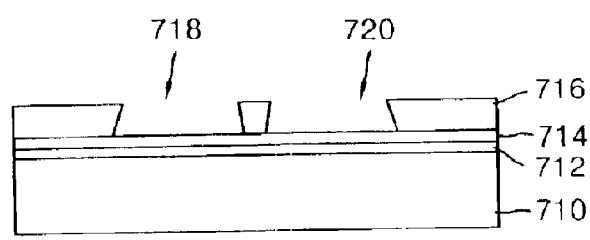

As shown in FIGS. 7c and 7d, the photoconductive epilayer 714 is cleaned before a photoresistor 716 is deposited on the cleaned photoconductive layer 714. The photoresistor 716 is patterned to form two electrode patterns 718 and 720 by etching the photoresistor 716 with a developer, e.g., AZ5214 using an image reversal photolithography. An electrode gap pattern is defined between the two electrode patterns 718 and 720 on an unetched photoresistor 716.

Figure 7E:
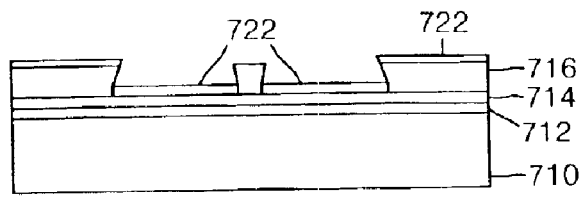
Figure 7F:
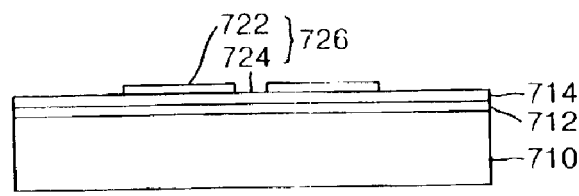

As a next step, as shown in FIG. 7e, a switch electrode 722 is formed on the switch electrode patterns 718 and 720 by depositing a metal according to the method of a evaporation or a sputtering. The metal deposited on the region other than the switch electrode pattern 718 and 720 are removed together with the photoresistor 716 by using a lift-off technique. Thereby, the photoconductive switch 726 with electrode gap 724 is fabricated.

Figure 7G:
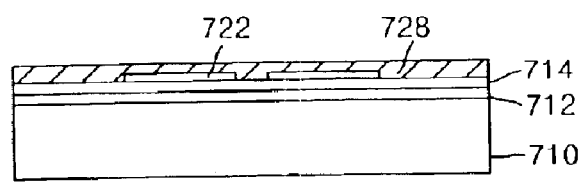
Figure 7H:
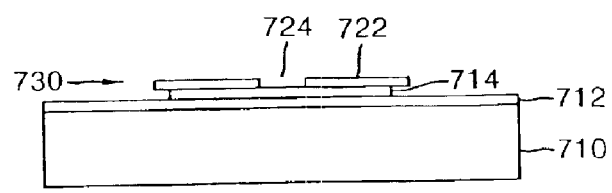

As shown in FIG. 7g, the photoresistor 728 is deposited on the photoconductive switch 726. Next, as shown in FIG. 7h, the photoconductive epilayer 714 is etched out except a desired photoconductive assembly 730. Herein, as the method for etching out the photoconductive epilayer 714 a dry etching technique by using plasma or a chemical etching using mixed solution including a diluted ammonium hydroxide acid($NH_4OH$) and hydrogen peroxide. When using the chemical etching method, the etching of the photoconductive epilayer 714 can be verified by rainbow color reflected on the scarifying layer 714 of which the refraction coefficient is lower than that of the substrate 710.

According to the process above, the photoconductive switch assembly 730 will have different patterns depending on each near-field probe shown in FIGS. 3 to 6. That is, provided that the photoconductive switch assembly 730 uses circular optical fiber as the optical waveguide, the photoconductive switch assembly 730 is formed as a circular figure when applied to the near-field probes of FIGS. 3 and 4, while the photoconductive switch assembly 730 is formed as an oval figure when applied to the near-field probes of FIGS. 5 and 6.

Figure 7I:
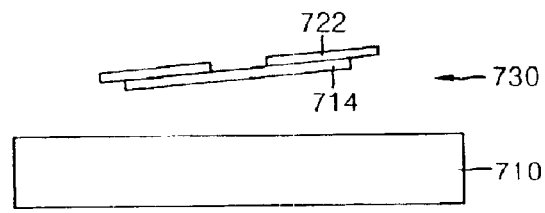

Next, as shown in FIG. 7i, the photoconductive switch assembly 730 is detached from the substrate 710 by selectively etching the sacrificial layer 712 using a chemical etching solution. Herein, the chemical etching solution is selected depending on the material used as the sacrificial layer 712. For instance, diluted hydrofluoric acid(HF) solution is used when the sacrificial layer is of AlAs and diluted hydrochloric acid(HCL) is used when the sacrificial layer is of InP. The photoconductive switch assembly 730 detached from the substrate are then be preserved in Isopropyl Alcohol(IPA).

Figure 7J:
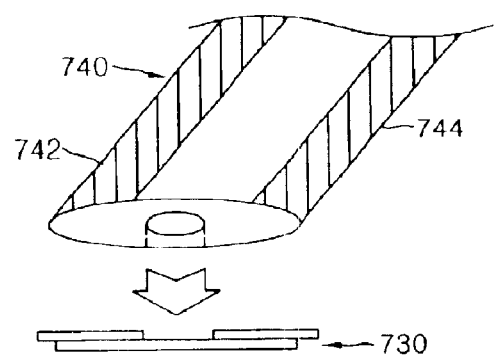

Next, as shown in FIG. 7j, the optical waveguide 740 of FIGS. 3 to 6 on which the stripe electrodes 742 and 744 are coated is associated with the photoconductive switch assembly 730, to form the near-field probe as shown in FIGS. 3 to 6. If the photoconductive switch assembly 730 is associated with the optical waveguide 320 and 420 of FIGS. 3 and 4, it functions as the near-field probe or the array probe; if the photoconductive switch assembly 730 is associated with the optical waveguide 520 of FIG. 5, it functions as the three-dimensional near-field probe; and if the photoconductive switch assembly 730 is associated with the optical waveguide 620 of FIG. 6, it functions as the very small three-dimensional near-field probe.

Figure 7K:
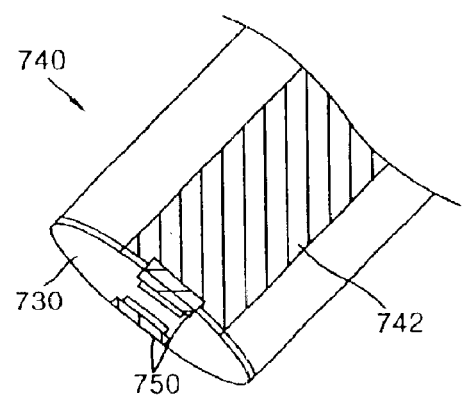

As a final step, as shown in FIG. 7k, by using a conductive adhesive such as the conductive epoxy, the two switch electrodes 722 of the photoconductive switch assembly 730 are electrically connected to the two stripe electrodes 742 and 744 coated on the optical waveguide 740 respectively, to finally constitute the near-field probe.

Figure 8A:
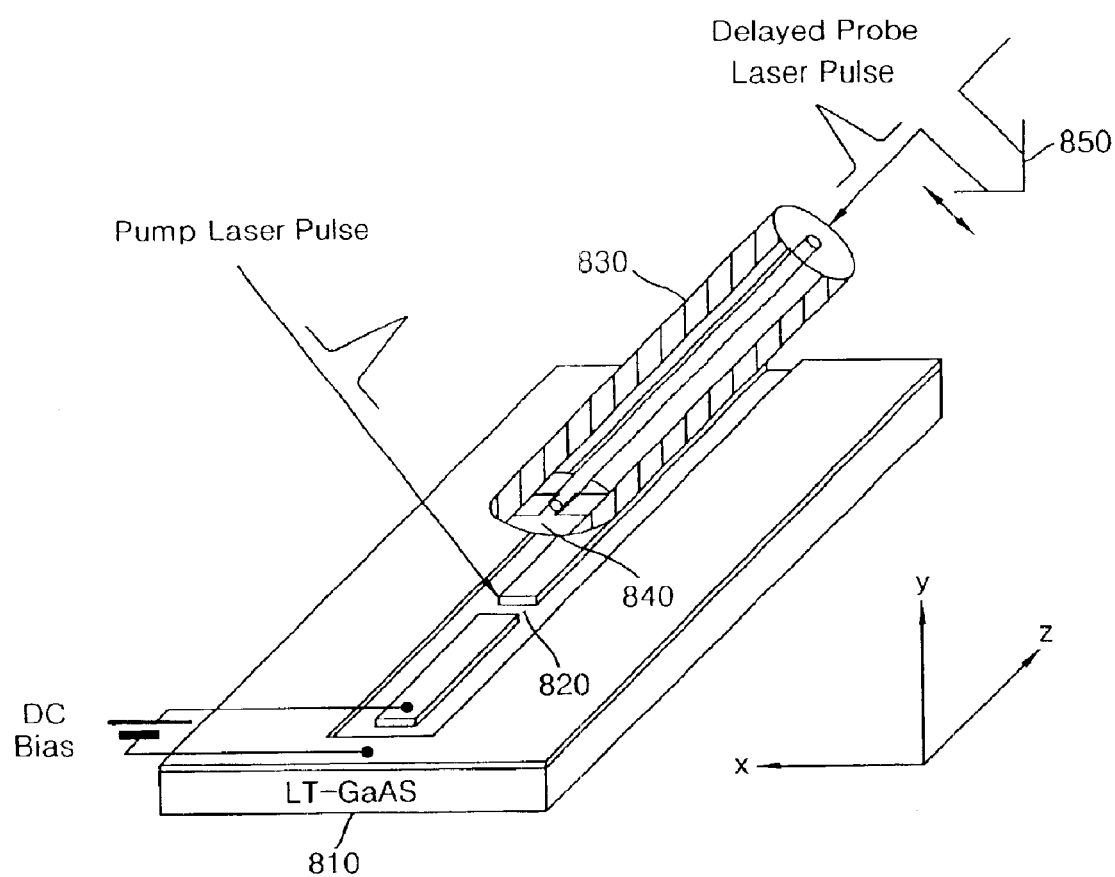
FIGS. 8a and 8b respectively exhibit exemplary probe positioning methods for measuring a transverse near electric-field component (X-direction) and a vertical near electric-field component (Y-direction) of an electromagnetic field.
Figure 8B:
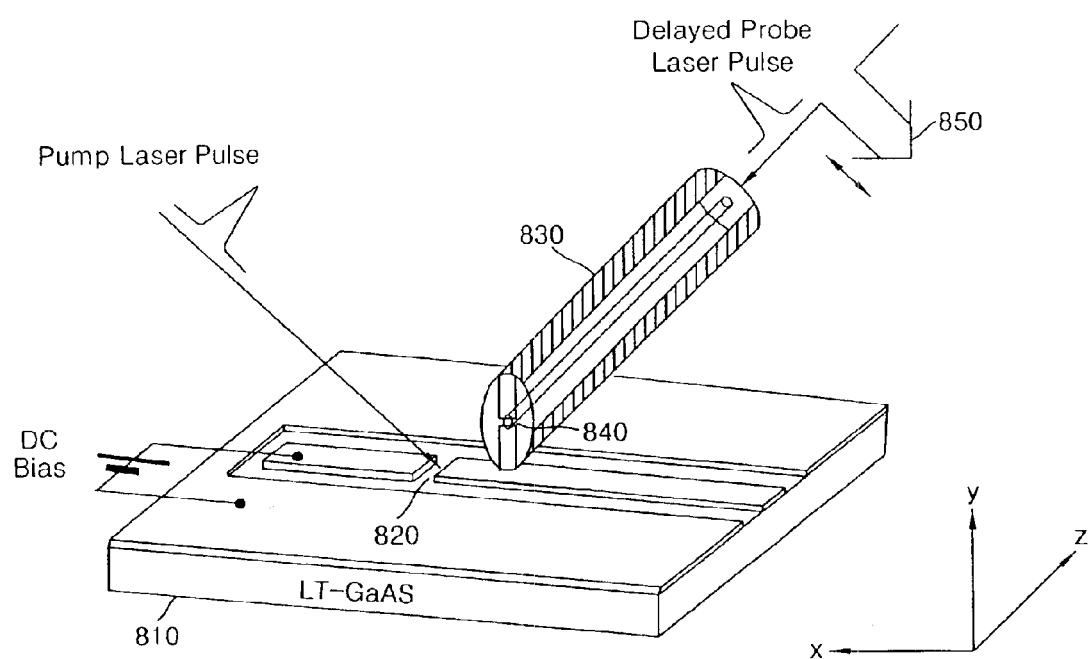

FIGS. 8a and 8b respectively exhibit exemplary probe positioning methods for measuring a transverse near electric-field component (X-direction) and a vertical near electric-field component (Y-direction) of an electromagnetic field originated from the DUT when the DUT is introduced to the pump laser pulse beam when the near-field probe is provided.

Referring now to FIG. 8a, the photoconductive switch 820 associated with a coplanar waveguide(CPW) is formed on the ultrafast photoconductive body 810. The probe in accordance with the present invention is capable of measuring the transverse near electric-field component (X-directional component) generated by a picosecond pulse propagating on the coplanar waveguide. If a pump laser pulse beam is introduced to the photoconductive switch 820 to which DC bias has been applied, a picosecond electrical pulse signal is generated. When a probe laser pulse beam having delayed at the optical delay-line 850 is introduced to the end point of the near-field probe 830 through the optical waveguide, carriers generated at the photoconductive switch 840 are forced to move by a transverse component at the measurement point, which leads to measurement of the transverse component at the measurement point near the coplanar waveguide.

The longitudinal component (Z-directional component) can be measured in the state that the probe is rotated clockwise by 90 degrees (the photoconductive switch 840 of the probe is positioned in parallel with the measured surface of the DUT or in the Z-direction) from the configuration for measurement of the transverse component shown in FIG. 8a (the photoconductive switch 840 of the probe is positioned in parallel with the measured surface of the DUT or in the X-direction). On the contrary, FIG. 8b illustrates a state for measuring the normal field component, and therefore, the photoconductive switch 840 is located in the perpendicular direction with the measured surface of the DUT.

The near-field probe in accordance with the present invention is capable of separately measuring near-field components of electrical signals existing near the region of interest above the DUT by scanning the region of interest of the DUT using an electronically controlled two-dimensional or three-dimensional scanning system and finally forming a map of the three-dimensional field components resulting from the electrical signal propagating on the DUT.

As described above, in accordance with the near-field probe of the present invention, sub-picosecond temporal resolution can be achieved by employing the ultrafast photoconductive switch, the space between the photoconductive switches can be limited to sub-micron, and sub-micron spatial resolution can be implemented by utilizing a single-mode optical waveguide according to a laser wavelength.

In addition, a high sensitivity of measurement can be achieved since the DUT can be measured by the movement of the carriers generated by the laser beam and having sub-picosecond lifetime, and therefore, less affected by a noise source.

Moreover, a so-called loading effect can be minimized since the carriers generated by the laser beam degenerate in sub-picoseconds and the ultrafast photoconductive epilayer with thickness of 100 nanometers to 2 micrometers is detached and transplanted by using the epitaxial lift-off (ELO) technique.

While the invention has been shown and described with respect to the preferred embodiments, it will be understood by the skilled in the art that various changes and modifications may be made without departing from the spirit and scope of the invention as defined in the following claims.

What is claimed is:

1. A near-field probe driven by a short laser pulse delayed through an optical delay-line for detecting vectors of near-field components of electrical signals propagating through a device under test including an electrical device or an electronic circuit based on a sampling principle, comprising:

a photoconductive switch assembly including a thin semiconductor photoconductive body, at least two separated switch electrodes formed on the thin semiconductor photoconductive body, and an electrode gap formed between the two separated switch electrodes; and an optical waveguide attached to one side of the photoconductive switch assembly by using an optical adhesive, wherein the optical waveguide is partially coated with conductive material on the outer surface thereof, wherein the conductive material forms at least two stripe electrodes in the longitudinal direction of the optical waveguide, and the stripe electrodes are electrically connected to each other with the switch electrodes and a core of the optical waveguide is optically aligned with the electrode gap.

2. The near-field probe as claimed in claim 1, wherein the cross-section of the optical waveguide is a circle or a rectangle and one end of the optical waveguide is cut to form a cross-section of a circle or a rectangle, or cut with inclination having prescribed angle to form an oval.

3. The near-field probe as claimed in claim 2, wherein the prescribed angle is around 45 degrees.

4. The near-field probe as claimed in claim 3, wherein the near-field probe is capable of providing map of 2-dimensional or 3-dimensional near-field components.

5. The near-field probe as claimed in claim 1, wherein one end of the optical waveguide is tapered within a range of a tapering angle to form a bevel-edge.

6. The near-field probe as claimed in claim 5, wherein the tapering angle is smaller than or equal to 45 degrees.

7. The near-field probe as claimed in claim 5, wherein a tip of the bevel-edge is cut to form a inclined cross-section with a prescribed angle.

8. The near-field probe as claimed in claim 7, wherein the prescribed angle is around 45 degrees.

9. The near-field probe as claimed in claim 1, wherein the photoconductive switch assembly, one end of which a face where the switch electrodes are formed or the other end face, is connected to one end of the optical waveguide.

10. The near-field probe as claimed in claim 1, wherein the thin semiconductor photoconductive body has a picosecond or shorter lifetime of carriers and is a material that is capable of absorbing wavelengths of the short laser pulse.

11. The near-field probe as claimed in claim 10, wherein the wavelength of the short laser pulse is shorter than or equal to 840 nanometers, and the material that is capable of absorbing the wavelengths of the short laser pulse is LT-GaAs or SOS.

12. The near-field probe as claimed in claim 11, wherein the short laser pulse is generated by mode-locked Ti:Sapphire laser or mode-locked optical fiber pulse laser.

13. The near-field probe as claimed in claim 10, wherein the wavelength of the short laser pulse is shorter than or equal to 1.6 micrometers, and the material that is capable of absorbing the wavelengths of the short laser pulse is InGaAs.

14. The near-field probe as claimed in claim 13, wherein the short laser pulse is generated by mode-locked optical fiber pulse laser.

15. The near-field probe as claimed in claim 1, wherein the optical waveguide includes an optical fiber or dielectric optical waveguide, both having a core in the center thereof.

16. The near-field probe as claimed in claim 15, wherein a refraction coefficient of the optical waveguide is smaller than the refraction coefficient of the semiconductor thin photoconductive body.

17. The near-field probe as claimed in claim 1, wherein the conductive material coated on the optical waveguide includes a deposited metal or a conductive epoxy.

18. The near-field probe as claimed in claim 1, wherein the optical adhesive is a ultraviolet adhesive allowing the short laser pulse to transmit therethrough, and the refraction coefficient of the optical adhesive is smaller than the refraction coefficient of the semiconductor thin photoconductive body and larger than the refraction coefficient of the optical waveguide.

19. The near-field probe as claimed in claim 1, wherein the near-field probe is capable of providing map of 2-dimensional or 3-dimensional near-field components.

20. The near-field probe as claimed in claim 1, wherein the near-field probe radiates terahertz electromagnetic wave by applying DC voltage to the parallel stripe electrodes and by introducing short laser pulse.

21. The near-field probe as claimed in claim 20, wherein the near-field probe performs measurement and imaging of the terahertz electromagnetic wave.

22. The near-field probe as claimed in claim 21, wherein the near-field probe measures a near-field component or a far field component of the terahertz electromagnetic wave.

* * * * *